United States Patent
Kujacznski et al.

(10) Patent No.: US 9,228,957 B2
(45) Date of Patent: Jan. 5, 2016

(54) HIGH SPEED METHOD AND SYSTEM FOR INSPECTING A STREAM OF PARTS

(71) Applicant: GII ACQUISITION, LLC, Davisburg, MI (US)

(72) Inventors: Nathan Andrew-Paul Kujacznski, Flint, MI (US); James W. St. Onge, Bloomfield Hills, MI (US); Michael G. Nygaard, Fenton, MI (US)

(73) Assignee: GII ACQUISITION, LLC, Davisburg, MI (US)

( * ) Notice: Subject to any disclaimer, the term of this patent is extended or adjusted under 35 U.S.C. 154(b) by 0 days.

(21) Appl. No.: 14/449,361

(22) Filed: Aug. 1, 2014

(65) Prior Publication Data

US 2014/0346097 A1    Nov. 27, 2014

Related U.S. Application Data (63) Continuation-in-part of application No. 14/221,410, filed on Mar. 21, 2014, now Pat. No. 8,993,914, which is a continuation-in-part of application No. 13/901,868, filed on May 24, 2013.

(51) Int. Cl.
*B07C 5/00* (2006.01)
*G01N 21/89* (2006.01)
(Continued)

(52) U.S. Cl.
CPC .......... *G01N 21/89* (2013.01); *B07C 5/342* (2013.01); *B07C 5/3422* (2013.01); *G01N 21/8901* (2013.01); *G01N 2021/845* (2013.01)

(58) Field of Classification Search
CPC ............ B07C 5/02; B07C 5/34; B07C 5/3416

USPC .................................. 209/576, 579, 587, 938
See application file for complete search history.

(56) References Cited

U.S. PATENT DOCUMENTS 2,645,343 A    7/1953  Nemir
3,770,969 A *  11/1973 Ansevin ............ G01N 21/9045
                                                209/526

(Continued)

FOREIGN PATENT DOCUMENTS

WO    2005022076 A2    3/2005
WO    2009130062 A1    10/2009

OTHER PUBLICATIONS

International Search Report and Written; International application No. PCT/US14/16662; date of mailing Dec. 8, 2014.

(Continued)

*Primary Examiner* — Terrell Matthews
(74) *Attorney, Agent, or Firm* — Brooks Kushman P.C.

(57) ABSTRACT

A high-speed method and system for inspecting a stream of parts using at least one transparent traveling carrier of a conveyor subsystem are provided. The subsystem has a forward reach and a return reach. The method includes controllably receiving a stream of parts in rapid succession on the at least one traveling carrier and utilizing the subsystem to transfer the stream of parts in rapid succession to a part inspection station. The bottom surface of each part is illuminated through its traveling carrier with radiant energy when the part is located at the inspection station to generate reflected radiation signals which travel through its traveling carrier. A bottom image of each illuminated bottom surface is formed from the reflected radiation signals at an imaging location between the forward and return reaches at the inspection station. The bottom images are detected at the imaging location.

23 Claims, 9 Drawing Sheets

(51) Int. Cl.
*B07C 5/342* (2006.01)
*G01N 21/84* (2006.01)

(56) References Cited

U.S. PATENT DOCUMENTS

| | | | |
|---|---|---|---|
| 3,924,953 A | 12/1975 | Allard | |
| 4,239,969 A | 12/1980 | Haas et al. | |
| 4,315,688 A | 2/1982 | Pryor | |
| 4,547,674 A | 10/1985 | Pryor et al. | |
| 4,598,998 A | 7/1986 | Kamei et al. | |
| 4,644,394 A | 2/1987 | Reeves | |
| 4,721,388 A | 1/1988 | Takagi et al. | |
| 4,831,251 A | 5/1989 | Hanna | |
| 4,852,983 A | 8/1989 | Fein | |
| 4,906,098 A | 3/1990 | Thomas et al. | |
| 4,923,066 A | 5/1990 | Ophir et al. | |
| 4,969,746 A | 11/1990 | McConnell et al. | |
| 4,970,401 A | 11/1990 | Sadeh et al. | |
| 4,983,043 A | 1/1991 | Harding | |
| 5,012,117 A | 4/1991 | Karafa et al. | |
| 5,024,529 A | 6/1991 | Svetkoff et al. | |
| 5,098,031 A | 3/1992 | Hitomi | |
| 5,164,995 A | 11/1992 | Brooks et al. | |
| 5,168,458 A | 12/1992 | Gomes | |
| 5,170,306 A | 12/1992 | Gomes | |
| 5,291,272 A | 3/1994 | Demirsu | |
| 5,383,021 A | 1/1995 | Hanna | |
| 5,431,289 A * | 7/1995 | Hoffman | B07C 5/366 198/494 |
| 5,521,707 A | 5/1996 | Castore et al. | |
| 5,531,316 A | 7/1996 | Savino | |
| 5,546,189 A * | 8/1996 | Svetkoff | G01B 11/24 250/559.23 |
| 5,568,263 A | 10/1996 | Hanna | |
| 5,608,530 A | 3/1997 | Gates | |
| 5,617,209 A | 4/1997 | Svetkoff et al. | |
| 5,646,724 A | 7/1997 | Hershline | |
| 5,751,833 A * | 5/1998 | Blit | B07C 5/3422 209/576 |
| 5,815,275 A | 9/1998 | Svetkoff et al. | |
| 5,847,382 A | 12/1998 | Koch et al. | |
| 6,046,462 A | 4/2000 | Yokajty et al. | |
| 6,055,329 A | 4/2000 | Mufti | |
| 6,064,756 A * | 5/2000 | Beaty | G06T 7/0002 250/559.23 |
| 6,098,031 A | 8/2000 | Svetkoff et al. | |
| 6,252,661 B1 | 6/2001 | Hanna | |
| 6,285,034 B1 | 9/2001 | Hanna et al. | |
| 6,289,600 B1 | 9/2001 | Watts | |
| 6,313,948 B1 | 11/2001 | Hanna | |
| 6,542,580 B1 * | 4/2003 | Carver | G01V 5/0008 378/57 |
| 6,959,108 B1 | 10/2005 | Bartelt et al. | |
| 7,134,544 B1 | 11/2006 | Kilper et al. | |
| 7,312,607 B2 | 12/2007 | Nygaard | |
| RE39,978 E * | 1/2008 | Bieman | G01B 11/2522 250/237 G |
| 7,363,817 B2 | 4/2008 | Bond et al. | |
| 7,403,872 B1 | 7/2008 | St. Onge et al. | |
| 7,633,046 B2 | 12/2009 | Spalding | |
| 7,633,634 B2 | 12/2009 | Spalding et al. | |
| 7,633,635 B2 | 12/2009 | Nygaard et al. | |
| 7,684,054 B2 | 3/2010 | Crowther | |
| 7,738,088 B2 | 6/2010 | Spalding | |
| 7,738,121 B2 | 6/2010 | Spalding | |
| 7,755,754 B2 | 7/2010 | Spalding | |
| 7,777,900 B2 | 8/2010 | Nygaard et al. | |
| 7,796,278 B2 | 9/2010 | Spalding et al. | |
| 7,812,970 B2 | 10/2010 | Nygaard | |
| 7,920,278 B2 | 4/2011 | Nygaard | |
| 8,054,460 B2 | 11/2011 | Agapiou et al. | |
| 8,179,434 B2 | 5/2012 | Koval et al. | |
| 8,228,493 B2 | 7/2012 | Yagyu et al. | |
| 8,390,826 B2 | 3/2013 | Walstra | |
| 8,416,403 B2 | 4/2013 | Nygaard | |
| 8,570,504 B2 | 10/2013 | Nygaard | |
| 8,615,123 B2 | 12/2013 | Dabic | |
| 2001/0021026 A1 | 9/2001 | Liu | |
| 2003/0034227 A1 * | 2/2003 | Gerber | B65G 47/847 198/473.1 |
| 2005/0174567 A1 | 8/2005 | Hanna | |
| 2006/0236792 A1 * | 10/2006 | Hanna | G01B 5/18 73/865.8 |
| 2007/0223009 A1 | 9/2007 | Erfling et al. | |
| 2009/0103107 A1 | 4/2009 | Nygaard | |
| 2009/0103112 A1 | 4/2009 | Nygaard | |
| 2009/0107896 A1 | 4/2009 | Gochar, Jr. | |
| 2010/0084245 A1 | 4/2010 | Gonzalez Alemany et al. | |
| 2010/0201806 A1 | 8/2010 | Nygaard et al. | |
| 2010/0245850 A1 | 9/2010 | Lee et al. | |
| 2011/0005899 A1 | 1/2011 | Grzelak | |
| 2012/0105429 A1 | 5/2012 | Nygaard | |
| 2012/0285751 A1 | 11/2012 | Turner | |
| 2012/0293623 A1 | 11/2012 | Nygaard | |
| 2012/0293789 A1 | 11/2012 | Nygaard | |
| 2012/0303157 A1 | 11/2012 | Chung | |
| 2013/0235371 A1 | 9/2013 | Nygaard et al. | |
| 2013/0258046 A1 * | 10/2013 | Nygaard | G06T 7/0004 348/36 |
| 2014/0043610 A1 | 2/2014 | Engel et al. | |
| 2014/0063509 A1 | 3/2014 | Nygaard et al. | |
| 2014/0168661 A1 | 6/2014 | Nygaard et al. | |

OTHER PUBLICATIONS

Notice of Allowance and Fee(S) Due; U.S. Appl. No. 14/221,410; date of mailing Dec. 5, 2014.

International Search Report and Written Opinion, International application No. PCT/US2014/016663; date of mailing May 28, 2014.

International Search Report and Written Opinion; International application No. PCT/US2015/016307; date of mailing Jun. 3, 2015.

Brosed, Francisco Javier, et al.; 3D Geometrical Inspection of Complex Geometry Parts Using a Novel Laser Triangulation Sensor and a Robot; Sensors 2011, 11, 9-110; doi:10.3390/s110100090; published Dec. 23, 2010.

Yogeswaran, Arjun; 3D Surface Analysis for the Automated Detection of Deformations on Automotive Panels; Ottawa-Carleton Institute for Electrical and Computer Engineering School for Information Technology and Engineering, University of Ottawa; Apr. 2011.

International Search Report and Written Opinion; International application No. PCT/US15/34349; date of mailing Sep. 15, 2015.

* cited by examiner

HIGH SPEED METHOD AND SYSTEM FOR INSPECTING A STREAM OF PARTS

CROSS-REFERENCE TO RELATED APPLICATIONS

This application is a continuation-in-part of U.S. patent application entitled "HIGH-SPEED, HIGH-RESOLUTION, TRIANGULATION-BASED, 3-D METHOD AND SYSTEM FOR INSPECTING MANUFACTURED PARTS AND SORTING THE INSPECTED PARTS" filed on Mar. 21, 2014 and having U.S. Ser. No. 14/221,410. That application is a continuation-in-part of U.S. patent application entitled "HIGH-SPEED, TRIANGULATION-BASED, 3-D METHOD AND SYSTEM FOR INSPECTING MANUFACTURED PARTS AND SORTING THE INSPECTED PARTS" filed on May 24, 2013 and having U.S. Ser. No. 13/901,868.

TECHNICAL FIELD

At least one embodiment of the present invention relates to high-speed methods and systems for inspecting streams of parts and, in particular, to such methods and systems which utilize conveyor subsystems.

OVERVIEW

Traditional manual, gauging devices and techniques have been replaced to some extent by automatic inspection methods and systems. However, such automatic inspection methods and systems still have a number of shortcomings associated with them.

Many parts, such as valve spring retainers, rivets, washers, first draw caps for ammunition, nuts, valve seats and the like develop microscopic surface defects such as slight hollows or depressions made in hard even surfaces by a blow or pressure during the manufacturing process.

Jackets are traditionally produced in cup and draw operations. A shallow cup is formed from a sheet of metal in a cupping press. Dies and punches in the press blank out a disk of the sheet metal and simultaneously form it into a shallow cup. The basic requirements for cups are concentric wall thickness and relatively even tops. The jacket is ultimately trimmed to meet specifications.

A jacket that is not much taller than it is wide (some handgun bullets) can often be used directly from the cupping press if the initial sheet material's thickness is close to the desired jacket thickness. For rifle bullets where the jacket can be two or more times the diameter of the bullet in length, the cup must receive additional processing. This is performed by the draw operation.

In metalworking, drawing a part refers to stretching it under controlled conditions, while reducing the diameter. The control is provided by a die and punch set that maintains constant contact with the jacket walls, ensuring equal stresses at all points on the bullet and controlling concentricity. The draw operation targets the sidewalls of the cup. The resulting part looks like a metal test tube, with a rounded base.

In drawing, several dies may be used in conjunction with one punch. This progressive draw tooling is known as a die stack. The tooling designer must consider the reduction in wall thickness and diameter that the stack must produce. All the dies and the punch must make full contact with the jacket so that no unworked metal remains when the part exits the die stack.

In optical metrology, inter-reflection (i.e., double bounce or secondary reflection) poses a challenge for surface measurement of shiny objects. Due to specular reflections that can occur among concave surfaces or combinations of surfaces positioned near right angles to each other, the true desired laser lines are often obscured by inter-reflection lines. Such obscuration makes it difficult to measure shiny surfaces of complex surface geometry.

Some laser triangulation measuring equipment operates by projecting, with a laser beam having a wavelength centered at approximately 830 nm (infrared (IR) radiation), a light spot having a preset spot size onto the surface to be examined, e.g., from a laser projection "gun" that may be mounted normal to the surface being examined. A light detection unit including a lens and a light detecting element or "camera," such as a CCD or CMOS imaging chip or a position sensing device (PSD), e.g., of silicon, at an offset angle to the projection axis may observe the position of the laser spot in its field of view and output a signal describing the angle at which the spot appeared in the field of view. The range to the object can be computed from the angle information when the distance between the laser projection axis and the light detection unit is known. The offset angle between the laser beam and the line of sight of the light detection unit is often referred to as the "triangulation angle." Based on which part of the detector the light reflected from the imaged object impinges, the height or "z-component" of the object at the point at which the light spot impinges upon the object may be determined.

U.S. Pat. No. 7,403,872 discloses a method and system for inspecting manufactured parts such as cartridges and cartridge cases and sorting the inspected parts.

WO 2005/022076 discloses a plurality of light line generators which generate associated beams of light that intersect a part to be inspected.

U.S. Pat. No. 6,313,948 discloses an optical beam shaper for production of a uniform sheet of light for use in a parts inspection system having a light source including a coherent light generator, a diffractive beam shaper, and lens elements.

U.S. Pat. No. 6,285,034 discloses an inspection system for evaluating rotationally asymmetric workpieces for conformance to configuration criteria.

U.S. Pat. No. 6,252,661 discloses an inspection system for evaluating workpieces for conformance to configuration criteria.

U.S. Pat. No. 6,959,108 discloses an inspection system wherein workpieces to be inspected are consecutively and automatically launched to pass unsupported through the field of view of a plurality of cameras.

U.S. Pat. No. 4,831,251 discloses an optical device for discriminating threaded workpiece by the handedness by their screw thread profiles.

U.S. Pat. No. 5,383,021 discloses a non-contact inspection system capable of evaluating spatial form parameters of a workpiece to provide inspection of parts in production.

U.S. Pat. No. 5,568,263 also discloses a non-contact inspection system capable of evaluating spatial form parameters of a workpiece to provide inspection of parts in production.

U.S. Pat. No. 4,852,983 discloses an optical system which simulates the optical effect of traveling over a large distance on light traveling between reference surfaces.

U.S. Patent Application Publication No. 2005/0174567 discloses a system to determine the presence of cracks in parts.

U.S. Patent Application Publication No. 2006/0236792 discloses an inspection station for a workpiece including a conveyor, a mechanism for rotating the workpiece, and a probe.

U.S. Pat. No. 6,289,600 discloses a non-contact measuring device for determining the dimensions of a cylindrical object, such as a pipe.

U.S. Pat. No. 5,521,707 discloses a non-contact laser-based sensor guided by a precision mechanical system to scan a thread form producing a set of digitized images of the thread form.

WO 2009/130062 discloses a method and a device for the optical viewing of objects.

As described in U.S. Pat. No. 6,098,031, triangulation is the most commonly used 3-D imaging method and offers a good figure of merit for resolution and speed. U.S. Pat. Nos. 5,024,529 and 5,546,189 describe the use of triangulation-based systems for inspection of many industrial parts, including shiny surfaces like pins of a grid array. U.S. Pat. No. 5,617,209 shows a scanning method for grid arrays which has additional benefits for improving accuracy. The method of using an angled beam of radiant energy can be used for triangulation, confocal or general line scan systems. Unfortunately, triangulation systems are not immune to fundamental limitations like occlusion and sensitivity to background reflection. Furthermore, at high magnification, the depth of focus can limit performance of systems, particularly edge location accuracy, when the object has substantial relief and a wide dynamic range (i.e. variation in surface reflectance). In some cases, camera-based systems have been combined with triangulation systems to enhance measurement capability.

U.S. Pat. No. 5,098,031 discloses a method and system for high-speed, 3-D imaging of microscopic targets. The system includes confocal and triangulation-based scanners or subsystems which provide data which is both acquired and processed under the control of a control algorithm to obtain information such as dimensional information about the microscopic targets which may be "non-cooperative." The "non-cooperative" targets are illuminated with a scanning beam of electromagnetic radiation such as laser light incident from a first direction. A confocal detector of the electromagnetic radiation is placed at a first location for receiving reflected radiation which is substantially optically collinear with the incident beam of electromagnetic radiation. The triangulation-based subsystem also includes a detector of electromagnetic radiation which is placed at a second location which is non-collinear with respect to the incident beam. Digital data is derived from signals produced by the detectors.

U.S. Pat. No. 5,815,275 discloses triangulation-based 3-D imaging using an angled scanning beam of radiant energy.

U.S. Pat. Nos. 7,812,970 and 7,920,278 disclose part inspection using a profile inspection subsystem and triangulation.

U.S. Pat. No. 4,547,674 discloses a method and apparatus for inspecting gear geometry via optical triangulation.

U.S. Pat. No. 4,970,401 discloses a non-contact triangulation probe system including a base plate and a first non-contact triangulation probe including a light source mounted on a first movable slide.

U.S. Pat. Nos. 5,168,458 and 5,170,306 disclose methods and systems for gauging threaded fasteners to obtain trilobular parameters.

Other U.S. patent documents related to the invention include: U.S. Pat. Nos. 2,645,343; 4,315,688; 4,598,998; 4,644,394; 4,852,983; 4,906,098; 5,521,707; 5,608,530; 5,646,724; 5,291,272; 6,055,329; 4,983,043; 3,924,953; 5,164,995; 4,721,388; 4,969,746; 5,012,117; 7,363,817; 5,847,382; 6,046,462; 7,684,054; 7,403,872; 7,633,635; 7,312,607; 7,777,900; 7,633,046; 7,633,634; 7,738,121; 7,755,754; 7,738,088; 7,796,278; 7,684,054; 8,054,460; 8,179,434; 8,228,493; 8,416,403; 8,570,504; 8,615,123 and U.S. published patent applications 2010/0245850; 2010/0201806; 2012/0303157; 2012/0293623; 2014/0063509; 2014/0168661; and 2013/0235371.

SUMMARY OF EXAMPLE EMBODIMENTS

An object of at least one embodiment of the present invention is to provide a high-speed method and system for inspecting streams of parts using at least one transparent traveling carrier of a conveyor subsystem having upper and lower reaches wherein a bottom image of each part is formed and detected as an imaging location located between the upper and lower reaches.

In carrying out the above object and other objects of at least one embodiment of the present invention, a high-speed method of inspecting a stream of parts is provided. The method includes the steps of providing a conveyor subsystem having a forward reach and a return reach and including at least one traveling carrier. The method further includes controllably receiving a stream of parts in rapid succession on the at least one traveling carrier at a load station and utilizing the conveyor subsystem to transfer the stream of parts in rapid succession from the load station to a part inspection station at which a bottom surface of each part has a predetermined position and orientation for inspection and from the part inspection station to an unload station. The method further includes illuminating the bottom surface of each part through its traveling carrier with radiant energy when the part is located at the inspection station to generate reflected radiation signals which travel through its traveling carrier. A bottom image of each illuminated bottom surface is formed from the reflected radiation signals at an imaging location between the forward and return reaches at the inspection station. Each traveling carrier is substantially transparent to the radiant energy and the reflected radiation signals. The method further includes detecting the bottom images at the imaging location, processing the detected bottom images and removing the stream of parts at the unload station after inspection at the inspection station.

The processing of the detected bottom images may identify parts having an unacceptable defect. The method may further include the steps of directing parts not identified as having an unacceptable defect to an acceptable part area and directing parts identified as having an unacceptable defect to a defective part area whereby the inspected parts are sorted.

The subsystem may include a pair of spaced rollers including a drive roller and actuator assembly for rotatably driving the drive roller. The at least one traveling carrier may be a single, transparent, belt which is directed around the rollers when the actuator assembly drives the drive roller.

The actuator assembly may include a closed-loop servo motor coupled to the drive roller to rotate the drive roller at a substantially constant angular velocity.

The drive roller may have a resilient coating or sleeve which drivingly engages the belt. Each of the rollers may have a resilient coating or sleeve which engages the belt.

The rollers may include an idler roller spaced from the drive roller and the subsystem may include a take-up device coupled to the idler roller to pull the belt tight.

The belt may include a flexible glass belt having ends and a splice which joins or bonds the ends together.

The belt may include a flexible plastic belt having ends and a splice which joins or bonds the ends together.

The subsystem may include a pair of spaced rollers including a drive roller and an actuator assembly for rotatably driving the drive roller wherein the subsystem may further include at least one band and a plurality of discrete, spaced-apart, traveling carriers supported by the at least one band.

The conveyor subsystem may include at least one upper support for supporting a forward reach of the belt between the rollers and a lower support for supporting a lower reach of the belt between the rollers to resist vertical movement of the reaches.

The stream of parts may be a single-file stream of parts.

Still further in carrying out the above object and other objects of at least one embodiment of the present invention, a high-speed system for inspecting a stream of parts is provided. The system includes conveyor subsystem having a forward reach and a return reach and including at least one traveling carrier. The at least one traveling carrier controllably receives a stream of parts in rapid succession at a load station. The conveyor subsystem transfers the stream of parts in rapid succession from the load station to a part inspection station at which a bottom surface of each part has a predetermined position and orientation for inspection and from the part inspection station to an unload station. The system further includes an illuminator configured to illuminate the bottom surface of each part through its traveling carrier with radiant energy when the part is located at the inspection station to generate reflected radiation signals which travel through its traveling carrier. A lens and detector subsystem is configured to form a bottom image of each illuminated bottom surface from the reflected radiation signals at an imaging location between the forward and return reaches at the inspection station and configured to detect the bottom images at the imaging location. Each traveling carrier is substantially transparent to the radiant energy and the reflected radiation signals. At least one processor is configured to process the detected bottom images. At least one device is configured to remove the stream of parts from the conveyor subsystem at the unload station after inspection at the inspection station. A system controller is coupled to the conveyor subsystem to control the conveyor subsystem so that the at least one traveling carrier controllably receives and transfers the stream of parts in rapid succession.

The processing of the detected bottom images by the at least one processor may identify parts having an unacceptable defect. The system may further include a mechanism including a part sorter for directing parts not identified as having an unacceptable defect to an acceptable part area and directing parts identified as having an unacceptable defect to a defective part area. The system controller is coupled to the part sorter and the at least one processor to control the sorting based on the inspecting.

The conveyor subsystem may include a pair of spaced rollers including a drive roller and actuator assembly for rotatably driving the drive roller. The at least one traveling carrier may be a single, transparent belt which is directed around the rollers when the actuator assembly drives the drive roller.

The actuator assembly may include a closed-loop servo motor coupled to the drive roller to rotate the drive roller at a substantially constant angular velocity.

The drive roller may have a resilient coating or sleeve which drivingly engages the belt carrier. Each of the rollers may have a resilient coating or sleeve which engages the belt.

The rollers may include an idler roller spaced from the drive roller. The conveyor subsystem may include a take-up device coupled to the idler roller to pull the belt tight.

The belt may comprise a flexible glass belt having ends and a splice which joins or bonds the ends together.

The belt may comprise a flexible plastic belt having ends and a splice which joins or bonds the ends together.

The conveyor subsystem may include a pair of spaced rollers including a drive roller and an actuator assembly for rotatably driving the drive roller. The conveyor subsystem may include at least one band and a plurality of discrete, traveling carriers supported by the at least one band.

The conveyor subsystem may include a pair of spaced apart vacuum belts or bands and a plurality of discrete traveling carriers or slides supported between the belts or bands.

The conveyor subsystem may include at least one upper support for supporting a forward reach of the belt between the rollers and a lower support for supporting a lower reach of the belt between the rollers to resist vertical movement of the reaches.

The stream of parts may be a single-file stream of parts.

Other technical advantages will be readily apparent to one skilled in the art from the following figures, descriptions and claims. Moreover, while specific advantages have been enumerated, various embodiments may include all, some or none of the enumerated advantages.

DETAILED DESCRIPTION OF EXAMPLE EMBODIMENTS

As required, detailed embodiments of the present invention are disclosed herein; however, it is to be understood that the disclosed embodiments are merely exemplary of the invention that may be embodied in various and alternative forms. The figures are not necessarily to scale; some features may be exaggerated or minimized to show details of particular components. Therefore, specific structural and functional details disclosed herein are not to be interpreted as limiting, but merely as a representative basis for teaching one skilled in the art to variously employ the present invention.

Figure 1:
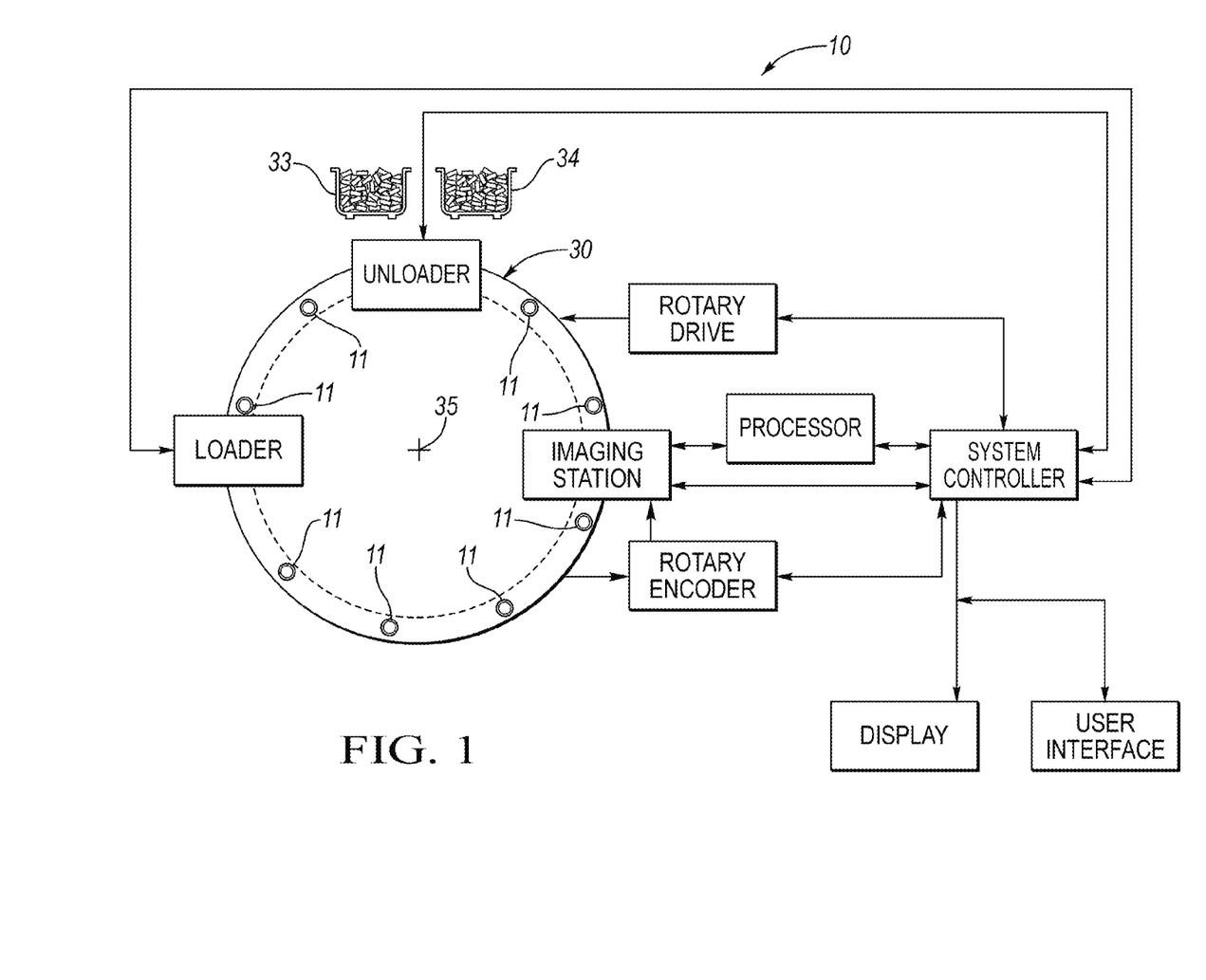
FIG. 1 is a schematic block diagram of a system constructed in accordance with the parent application of this application.

FIG. 1 (which corresponds to FIG. 6 of co-pending and co-owned U.S. patent application Ser. No. 14/221,410 filed Mar. 21, 2014) shows a high-speed, high-resolution triangulation-based, 3-D method and system for inspecting manufactured parts at one or more imaging stations and sorting the inspected parts. The parts, such as valve seats, washers, valve spring retainers, nuts, first draw caps for ammunition and rivets have top and bottom end surfaces which are optically inspected.

In general, one embodiment of the high-speed method and system of the present invention optically inspects manufactured parts such as the parts illustrated in FIGS. 7 through 15. The inspected parts are then typically sorted based on the inspection(s). The system, generally indicated at 10 in FIG. 1, is designed for the inspection of one or more outer end surfaces of the parts. The system 10 is suitable for the inspection of small, mass-produced manufactured parts. The subsystems of the system 10 which may be used for part handling and delivery may vary widely from application to application depending on part size and shape, as well as what inspections are being conducted. The subsystems ultimately chosen for part handling and delivery have some bearing on the nature of the subsystems conducting the optical and other non-contact inspection.

Initially, parts, such as first drawn caps 11 or valve spring retainers are placed into a source of parts such as an orienting feeder bowl (not shown) having a scalloped rim. The bowl is supported on an adjustable frame structure. Tooling around the rim takes advantage of the asymmetrical mass distribution of the parts to feed the parts onto a downwardly-sloped feeder conveyor or loader. Consequently, every part which exits the bowl is received by the conveyor and is properly oriented. One or more vibrators (not shown) controlled by a vibrator controller (not shown) vibrate the bowl to help move the parts in single file to a loading station for loading by a loader.

The system 10 typically includes a part transfer subsystem including a transfer mechanism, generally indicated at 30, and/or a transfer mechanism. The mechanism 30 is adapted to receive and retain parts thereon at the loading station at which the loader loads parts to be inspected from the bowl or other storage or transfer device. The transfer mechanism may include a slotted, flat track on which the parts 11 are conveyed to a bottom imaging or inspection station. The bottom imaging station typically includes a conveyor or some linear motion "pusher" type actuator having a linear encoder coupled to the conveyor to generate encoder signals and supply such signals to a sensor head and to a system controller. A slot of the track is dimensioned to allow focused and reflected lines of radiation to pass therethrough but not allow the parts 11 to fall therethrough as described hereinbelow. The conveyor may be a magnetic or vacuum conveyor for transferring parts to the transfer mechanism 30. Magnetic conveyors are frequently used to convey ferromagnetic articles, such as cans, stampings and the like. In conveyors of this type, permanent magnets are located in the frame of the conveyor beneath the conveying run of an endless belt and articles are attracted to the magnets so that the belt can travel along an incline or horizontal or vertical path of travel without the articles falling from the belt.

Alternatively, an indexing, beltless magnetic conveyor may be provided. Such a conveyor may include a housing defining a longitudinal length of the conveyor and a magnetic rack assembly moveably supported in the housing. The magnetic rack assembly includes a plurality of magnet assemblies supported at spaced intervals relative to one another along the longitudinal length of the conveyor. The beltless magnetic conveyor also includes a drive which is controlled by the system controller to index the magnetic rack assembly between a home or loading position proximate to one end of the housing and an end or inspection position which is proximate to an opposite end of the housing over the same path. The magnet assemblies are operable to generate a magnetic force which acts to attract ferromagnetic material toward the housing and to move the ferromagnetic material in the direction of the longitudinal length of the conveyor when the magnetic rack assembly is indexed.

The transfer mechanism 30 may be a rotating glass table or disk to transfer the retained parts so that the parts travel along a first path which extends from a loader at a loading station to a top inspection or imaging station at which the parts have a predetermined position and orientation for optical inspection. Subsequently, the transfer mechanism 30 transfers the parts after imaging at the imaging station so that the inspected parts travel along a second path which extends from the imaging station to an unloader at an unloading station at which the inspected parts are unloaded from the transfer mechanism 30 by the unloader. The loader and unloader may be the same device, which can place parts which "pass" the inspection in a "good part" bin 33 and place parts which don't "pass" the inspection in a "defective part" bin 34. The unloading station may be coincident with the loading station and the loading and unloading may be done manually or automatically.

The movable table or disk 30 may be a rotary index table or disk, for transferring parts at the top surfaces of the table 30. The table 30 is coupled to a rotary sensor or encoder which provides a control or encoder signal to the system controller and to a sensor head at the top imaging station at each of a plurality of known intervals of movement of the table 30. The control signals are utilized by the sensor head at the top imaging station as described hereinbelow. The rotary index table 30 typically has a central rotational axis 35 and an outer periphery which has a round shape. A rotary drive of the table 30 operates to rotate the index table 30 on a base for indexing rotation about the rotational axis 35 based on various sensor input signals from sensors to the system controller which, in turn, provides sequential control signals to a positioning drive mechanically coupled to the rotary drive. The system controller also provides control signals to a computer display and a part sorter or reject mechanism. The rotary drive drives the index table 30 between inspection stations such as machine vision and eddy current stations.

The parts may be dropped onto second track from the first track. As the parts 11 move down and exit the second track, they pass through the bottom imaging station to be inspected one at a time. The parts 11 which fail the inspection may be actively rejected by the part diverter or flipper. Parts which pass the inspection at the bottom imaging station are transferred to the rotary table 30 for top inspection.

A sensor head is located in both the top and bottom inspection stations. The sensor head is preferably a triangulation-based sensor head supported and mounted within each of the top and bottom imaging stations. Each sensor head illuminates either a top or bottom surface of each part 11 with focused planes or lines of radiation to obtain corresponding reflected lines when the part 11 is in the imaging station. The sensor heads sense their corresponding reflected lines to obtain corresponding 2-D profile signals.

As the parts 11 move through the imaging stations, corresponding sets of 2-D profile signals are generated by the sensor heads. At least one processor processes the sets of 2-D profile signals to obtain a 3-D view of each top or bottom surface of the part 11.

The system controller provides control signals based on the signals from the linear and rotary sensors or encoders. Alternatively or additionally, the signals from the rotary and linear encoders are directly utilized by the sensor heads at the top and bottom vision stations to control the sensor heads. The control signals are utilized to control the sensor heads which preferably have encoder inputs which allow precise control over the position of 2-D profile signals samples.

At least one signal processor may process the sets of 2-D profile signals to identify a defective part as described in greater detail hereinbelow. The at least one processor may process the sets of 2-D profile signals to obtain one or more measurements of the part.

Figure 2:
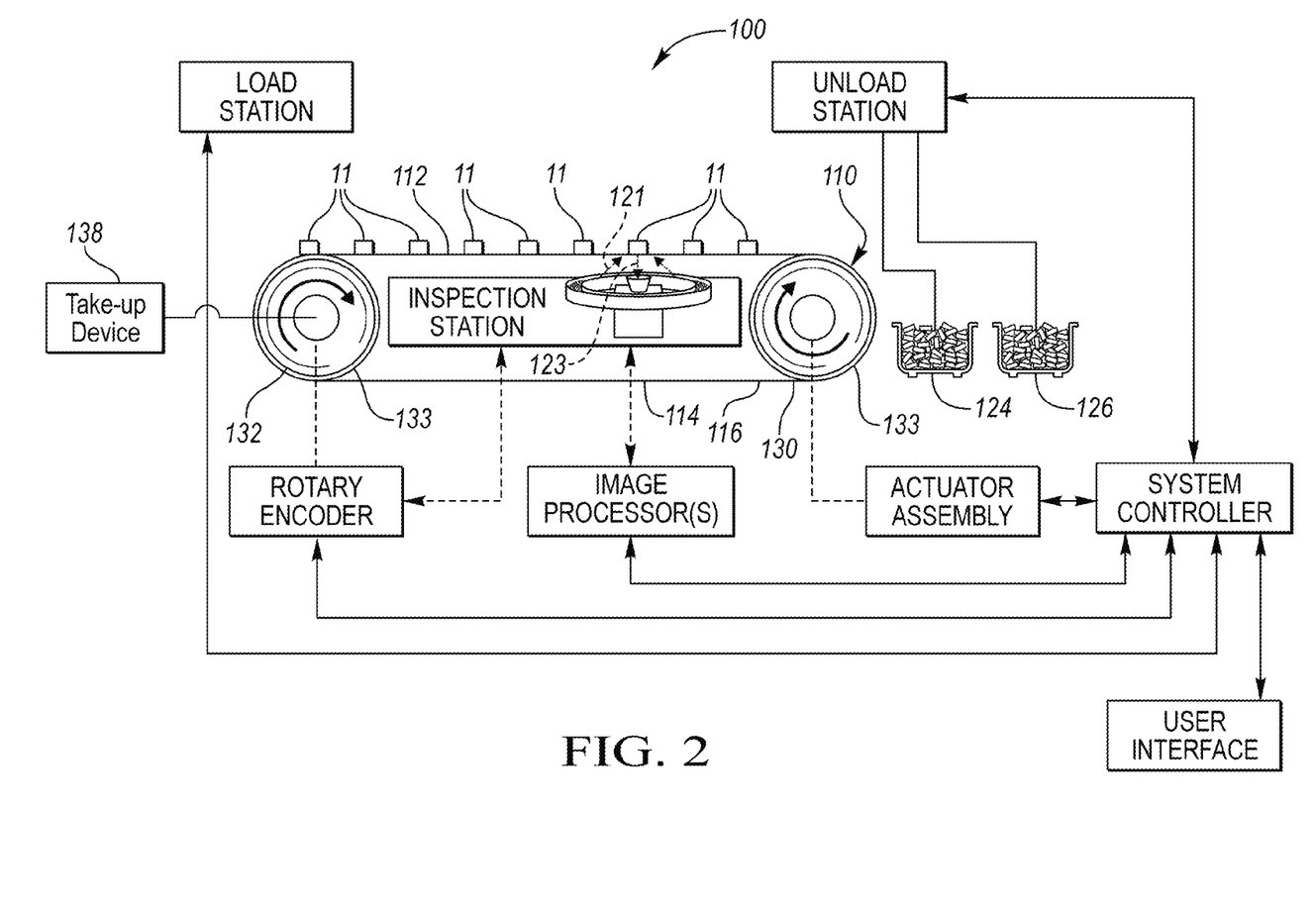
FIG. 2 is a schematic block diagram of a system constructed in accordance with at least one embodiment of the present invention.

Referring now to FIG. 2, there is illustrated a high-speed system, generally indicated at 100, for inspecting a stream of parts 11 such as the parts described with reference to FIG. 1. The system 100 includes a conveyor subsystem, generally indicated at 110, having a forward or upper reach 112 and a return or lower reach 114 and including at least one traveling carrier, in the form of an optically transparent, flexible glass or plastic belt, generally indicated at 116. The belt 116 controllably receives a stream of parts 11 in rapid succession at a load station. The conveyor subsystem 110 then transfers the stream of parts 11 in rapid succession from the load station to a part inspection station at which the bottom surface of each part 11 has a predetermined position and orientation on the belt 116 for inspection and then from the part inspection station to an unload station.

An illuminator 120 is configured to illuminate a bottom surface of each part 11 with radiant energy 121 through the transparent belt 116 when the part 11 is located at the inspection station to generate reflected radiation signals 123 which also travel through the transparent belt 116.

A lens and detector subsystem 122 (i.e. camera) is configured to form a bottom image of each illuminated bottom surface from the reflected radiation signals 123 at an imaging location between the forward and return reaches 112 and 114, respectively, at the inspection station. The belt 116 is substantially transparent to the radiant energy 121 and the reflected radiation signals 123. The subsystem 122 is configured to detect the bottom images at the imaging location.

At least one image processor is configured to process the detected bottom images. The processing of the detected bottom images by the processor identifies parts 11 having an unacceptable defect.

At least one device (such as the unloader of FIG. 1) is configured to remove the stream of parts 11 from the conveyor subsystem 110 at the unload station after inspection at the inspection station. A system controller is coupled to the conveyor subsystem 110 to control the conveyor subsystem 110 through an actuator assembly which may include a closed-loop servo motor coupled to a drive roller 130.

The system 100 may further include a mechanism including a part sorter (not shown) such as conventional blow off devices at the unload station for directing parts 11 not identified as having an unacceptable defect to an acceptable part area 124 and directing parts identified as having an unacceptable defect to a defective part area 126. The system controller is coupled to the part sorter at the unload station and the image processor to control the sorting based on the inspecting.

Preferably, the conveyor subsystem 110 is a linear conveyor subsystem 110 comprising a pair of spaced rollers 130 and 132 including the drive roller 130. The actuator assembly rotatably drives the drive roller 130. The belt 116 is a single, transparent belt 116 which is directed around the rollers 130 and 132 when the actuator assembly drives the drive roller 130.

The closed-loop servo motor coupled to the drive roller 130 rotates the drive roller 130 at a substantially constant angular velocity to coordinate the reception and the conveyance of the parts 11 in rapid succession.

The drive roller 130 (and the roller 132) preferably has a resilient coating or sleeve 133 which drivingly engages the belt 116.

The idler roller 132 is spaced from the drive roller 130 wherein the subsystem 110 preferably includes a take-up device 138 coupled to the idler roller 132 to pull the belt 116 tight.

Figures 3, 4, 5A, 5B:
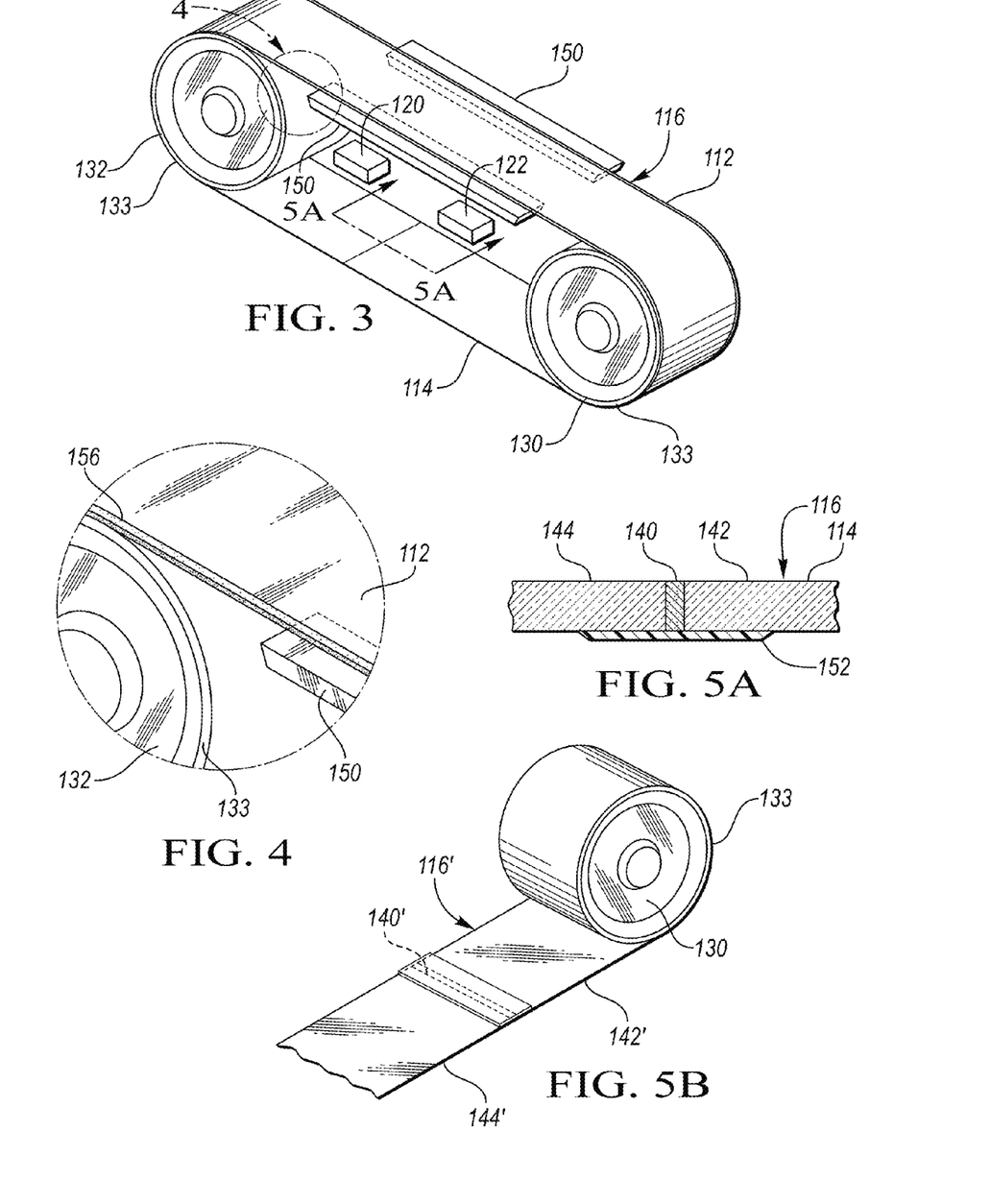
FIG. 3 is a schematic perspective view of parts of a conveyor subsystem of at least one embodiment of the present invention.
FIG. 4 is an enlarged view, taken within the phantom circle of FIG. 3, illustrating a thin, flexible, optically transparent, plastic or glass belt.
FIG. 5a is a view, partially broken away and in cross section, taken along lines 5a-5a of FIG. 3 showing a bonding or joining joint or splice.
FIG. 5b is a view similar to the view of FIG. 5a but showing a second such splice.
Figure 6:
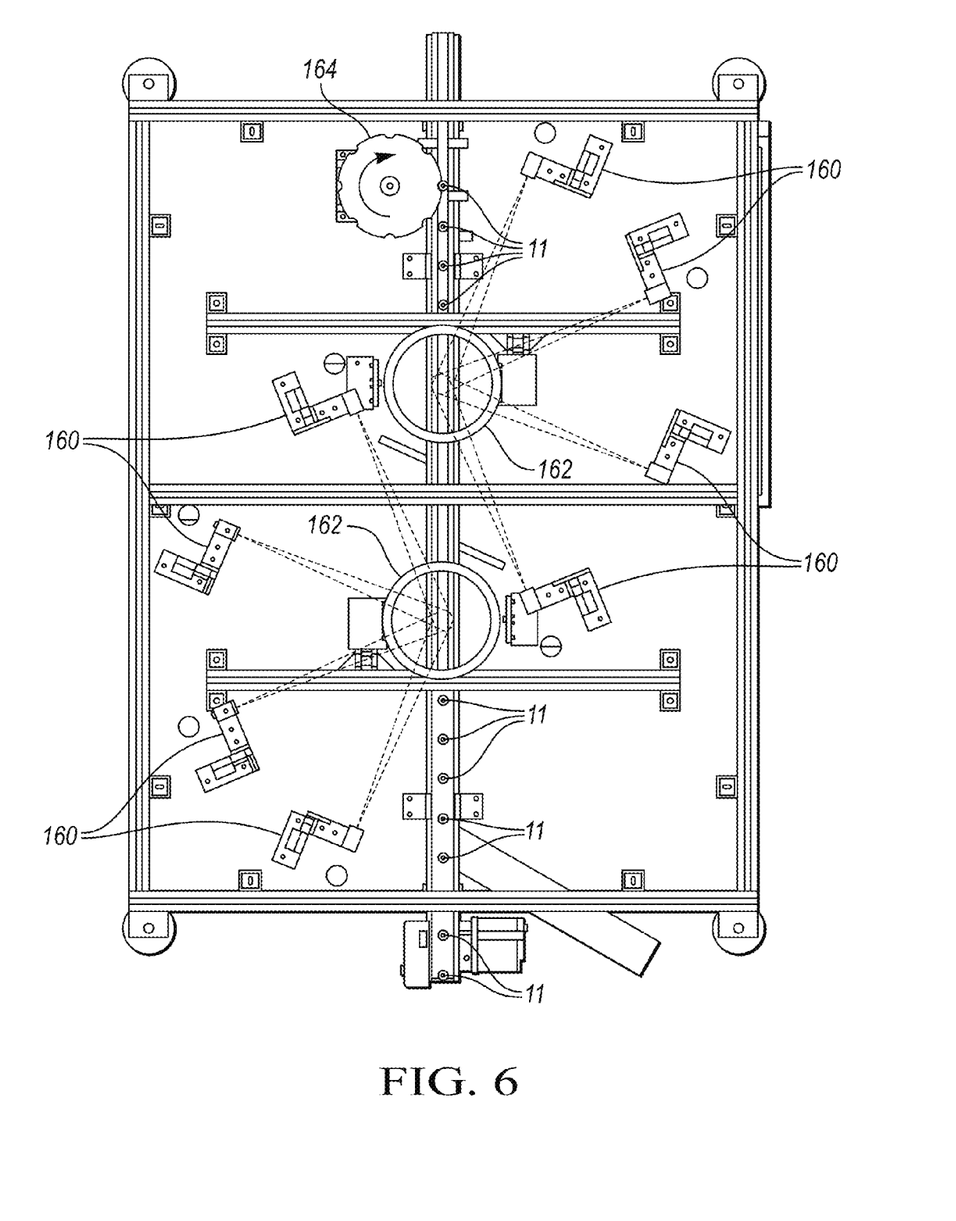
FIG. 6 is a top plan schematic view of the system including an 8-way side surface viewer at a pair of inspection systems.

The belt 116 may comprise a flexible glass belt in one embodiment of the invention. The belt 116 has a seam 140 at which ends 142 and 144 of the glass belt 116 are joined or bonded as shown in FIG. 5A. The seam 140 may be an adhesive. Alternatively, as shown in FIG. 5B, a splice such as provided by splice tape 140' may join ends 142' and 144' of glass belt 116'. The glass of the glass belts 116 and 116' may be flexible glass made by Corning, Inc. of Corning, N.Y. under the tradename Willow Glass. Other flexible glass providers include Nippon Electric Glass Co., Ltd. and Schott AG. Each glass is typically between 0.05 and 0.3 mm thick with a greater than 90% optical transmission and a bend radius of between 10-30 cm.

The belts 116 and 116' may comprise a flexible plastic belt having a seam or splice at which ends of the plastic belt are joined or bonded. The plastic of the plastic belt 116 or 116' may be clear polyester film such as Mylar or Lexar clear plastic film.

Figure 16:
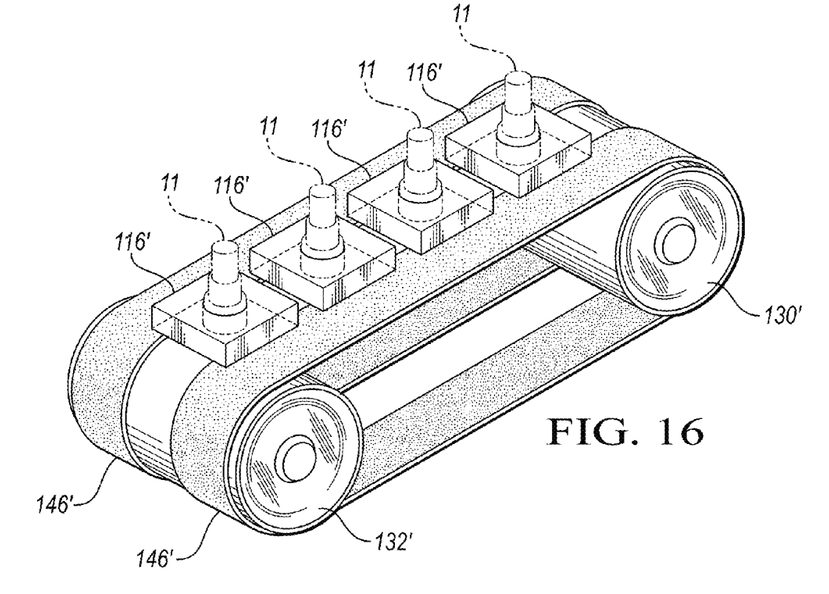
FIG. 16 is a view similar to the view of FIG. 3 but showing a different conveyor subsystem of another embodiment of the present invention.
Figure 17:
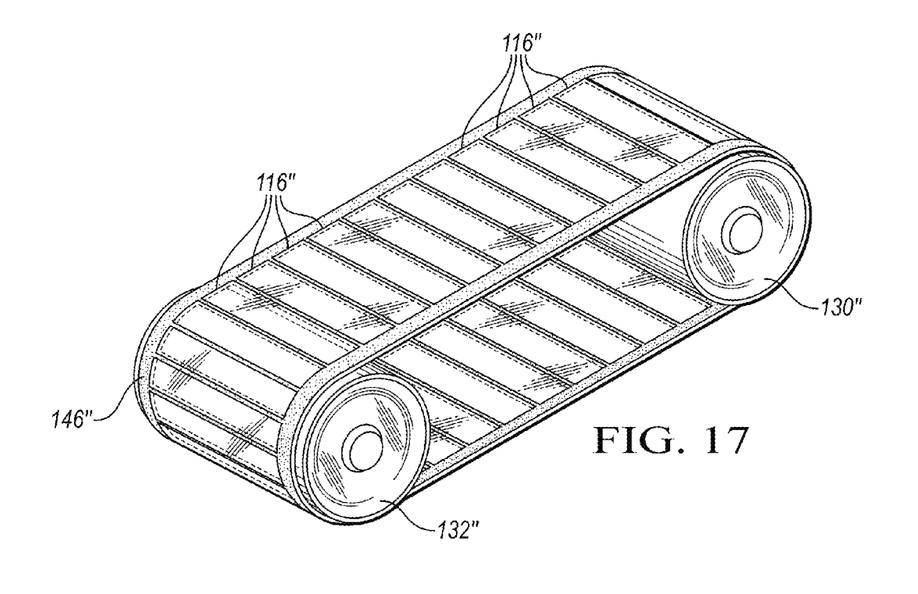
FIG. 17 is a view similar to the views of FIGS. 3 and 16 of yet another embodiment of a conveyor subsystem of the present invention.

As shown in FIGS. 16 and 17 the conveyor subsystem may include a pair of spaced rollers 130', 132' and 130", 132" respectively, including a drive roller 130' or 130" and an actuator assembly (not shown but the same or similar to the actuator assembly of FIG. 2) for rotatably driving the drive roller 130' or 130". The at least one traveling carrier includes a plurality of discrete, spaced-apart, transparent traveling carriers 116' or 116" on which the parts 11 are supported for inspection.

In the embodiment of FIG. 16, a plurality of clear glass or plastic carriers or slides 116' are supported on a pair of spaced bands 146'. For example, each band may be a vacuum belt, such as a stainless steel, apertured vacuum belt available from Belt Technologies, Inc. of Agawam, Mass. The belts 146' are spaced apart to allow the lens and detector subsystem to view the under surface of the parts 11 with the glass slides 116' held thereon by vacuum. The carriers or slides 116' may be picked up and placed on the belts 146' by a robot (not shown). The belts 146' have a plurality of vacuum holes or apertures 147' to hold the carriers 116' on the belts 146'.

In the embodiment of FIG. 17, a plurality of clear plastic or glass slats or carriers 116" are supported on a single band 146". In the embodiments of FIGS. 16 and 17, the bands 146' and 146" are driven by their respective drive rollers 130' and 130".

As shown in FIGS. 3 and 4, the conveyor subsystem 110 includes at least one upper, low friction support 150 (preferably two) for supporting the forward reach 112 between the rollers 130 and 132 and a lower support 152 (FIG. 5a) for supporting the lower or return reach 114 between the rollers 130 and 132 to resist vertical movement of the reaches 130 and 132. The supports 150 and 152 preferably support the glass belt 116 at handling tabs 156 (FIG. 4) affixed at opposite edges of the glass belt to minimize scratches, chips and fractures of the relatively brittle glass belt 116.

The illuminator 120 and the lens and detector subsystem 122 of FIG. 3 may be replaced by a high-speed, 2D/3D laser scanner (LJ-V7000 series) available from Keyence Corporation of Japan as explained in the above-noted parent application.

Referring now to FIGS. 6-9, an optional 6 or 8 (FIG. 6) way viewer provides side images from all around the parts 11 for a 360° view to find the smallest flaws in the outer side surfaces of the parts 11. Six (or 8) camera subsystems 160 with image analysis software that minimizes surface and lighting variations may be provided. A strobe LED ring light 162 illuminates the outer surfaces of the stream of parts at each vision station. Backlight lighting may provide data for dimensional analysis. Software is included for processing the side images.

Backlit lighting provides measurement of dimensional characteristics. It has the ability to measure maximum, minimum or average, simultaneously or separately: Radii, Concentricity, Straightness, Head space and length, neck, groove width, overall length, tapers etc.

Figure 7:
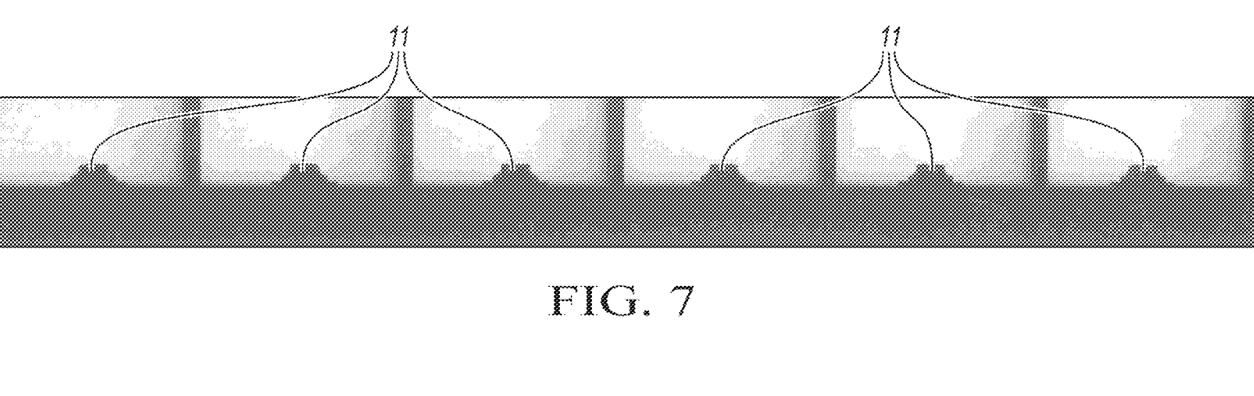
FIG. 7 shows six side views of a part at a pair of inspection stations.
Figure 8:
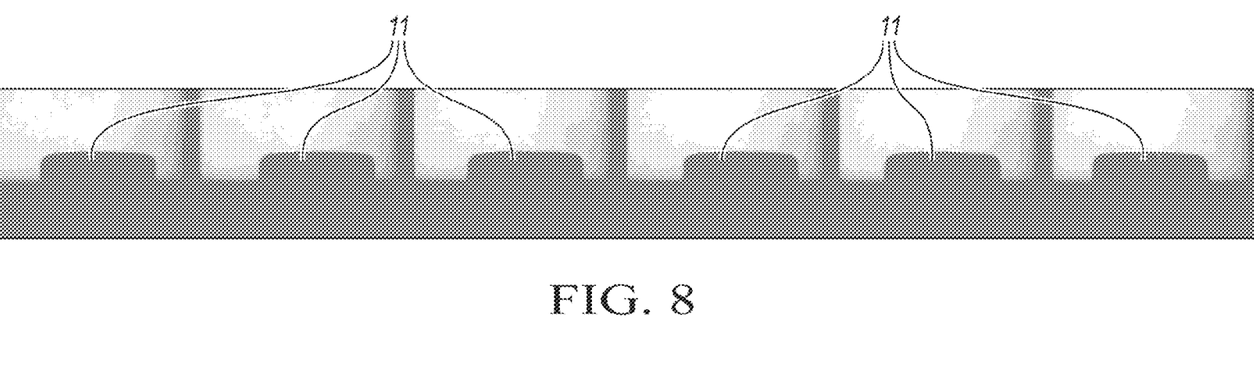
FIG. 8 shows six side views of a different part at the pair of inspection stations.
Figure 9:
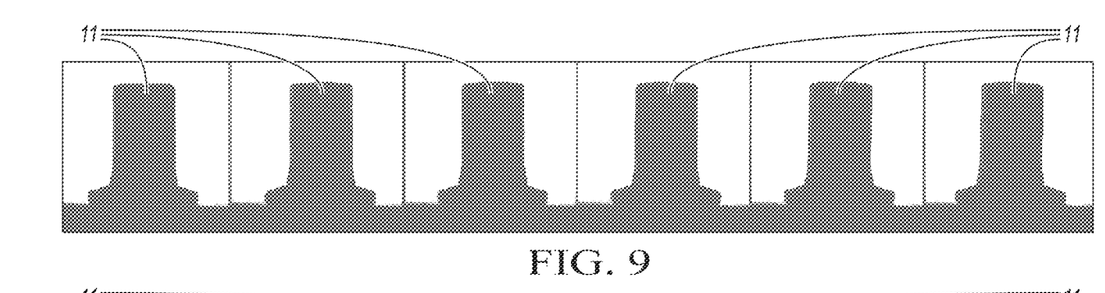
FIG. 9 shows six side views of a part at the pairs of inspection stations.

The first three images of FIG. 7 are from a first vision station and the second three images are from a second vision station. The six images are then combined in software to provide a 360° view.

Figure 10:
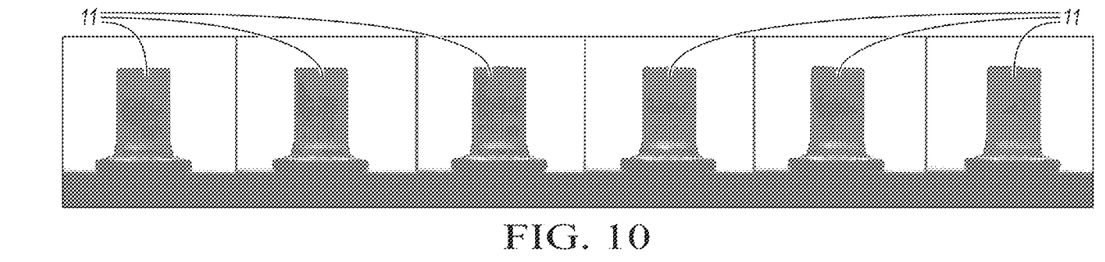
FIG. 10 shows six side views of a different part at the pairs of inspection stations.
Figure 11:
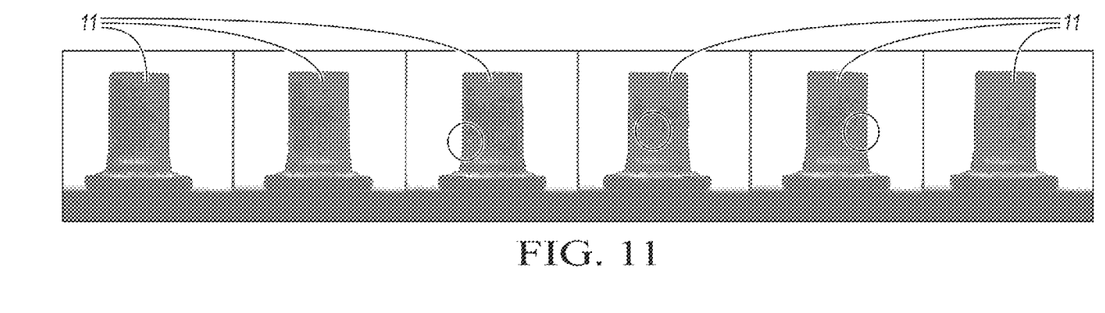
FIG. 11 shows six side views of a part at the pairs of inspection stations with a defect circled in three views.

Referring now to FIGS. 6 and 9-11, the optional 6 way viewer is similar to the previous viewer or, with the addition of frontlit lighting, to detect surface imperfections such as scratches, gouges, flakes, burrs, smears, discoloration, chips, cracks, dents. A good part is shown in FIG. 10 while a defective part is shown in FIG. 11 with the defect circled in multiple views.

Figure 12:
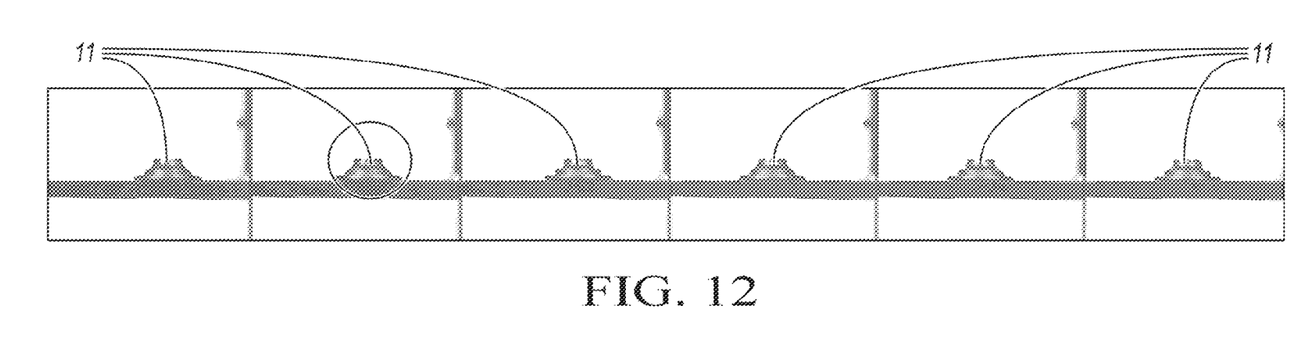
FIG. 12 shows six side views of a part at a pair of inspection stations with a defective part circled.
Figure 13:
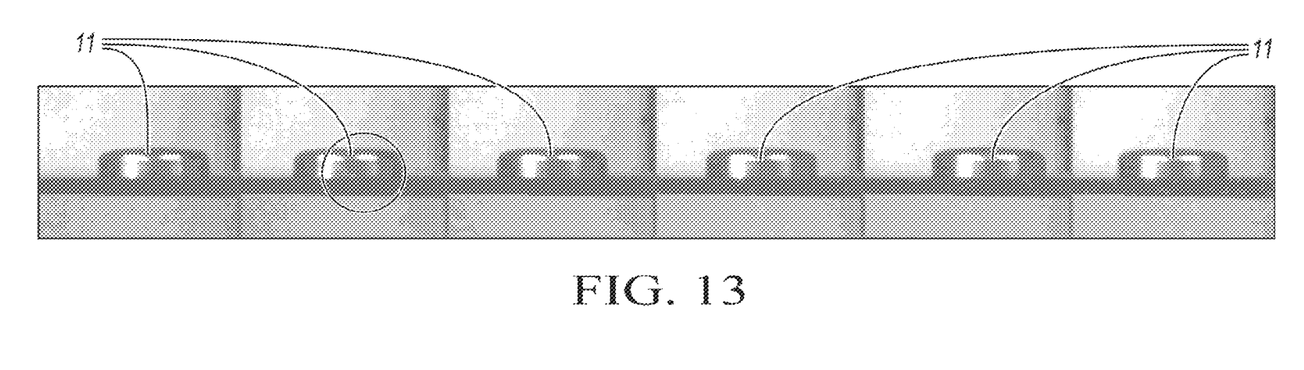
FIG. 13 shows six side views of a different part at a pair of inspection station with a defect circled.
Figure 14:
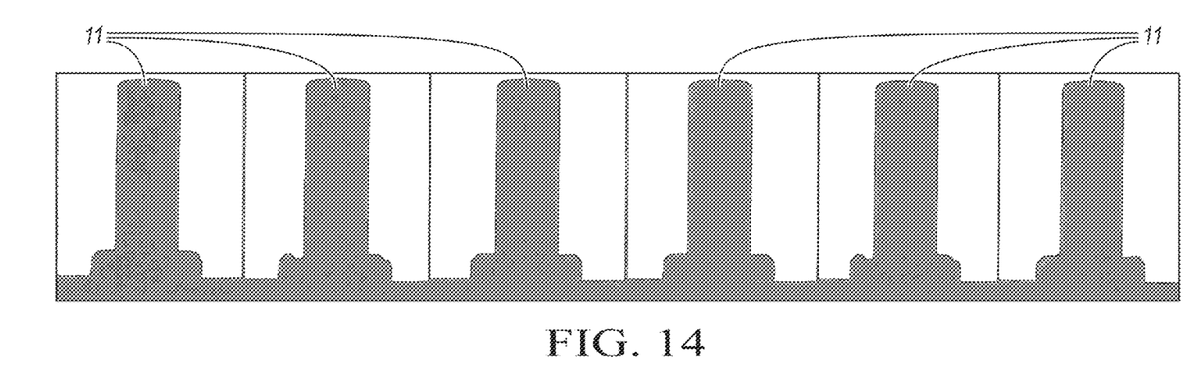
FIG. 14 shows six side views of a part at a pair of inspection stations.

In like fashion, frontlit lighting is used at the first vision station to show the circled defect in FIG. 12 and the circled defect in FIG. 13.

Figure 15:
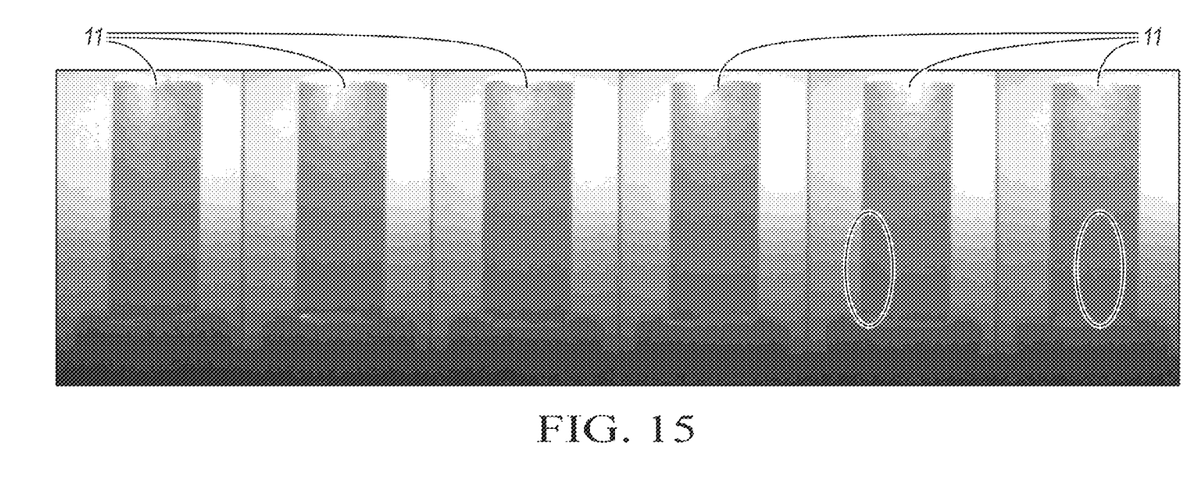
FIG. 15 shows six side views of a part at a pair of inspection stations with a defective part area circled.

In like fashion, a part in the form of a threaded bolt is illuminated and views taken as shown in FIGS. 11 and 15 with defects circled in the second image and the last two images of FIG. 15.

A method of at least one embodiment of the present invention, is as follows:

1. Receive a stream of parts such as ammunition caps in rapid succession such as from a metering wheel 164 (FIG. 6);
2. Transfer the stream of parts in rapid succession so that the stream of parts move along a path including an imaging or inspection station;
3. Support an illumination device and a camera or triangulation-based sensor head at the inspection station between the upper and lower reaches of the conveyor subsystem;
4. Deliver radiation generated by the illuminator or the sensor head to an exterior bottom surface of the moving part and sense the reflected radiation signals;
5. Process the signals;
6. Determine a part parameter or property using the signals;
7. Is part parameter or property within a range of acceptable values?
8. If "yes" accept part; and
9. If "no" reject part as being defective.

A "reject mechanism" or unloader in the inspection and sorting system can be implemented in a number of equivalent known embodiments. For example, a "reject mechanism" could remove a nonconforming workpiece in a number of ways, by (i) routing the workpiece on a conveyor to a bin for nonconforming parts, (ii) mechanically displacing the workpiece from a conveyor into a bin, such as by a flipper or pusher device, (iii) magnetically displacing a (ferrous) workpiece by selective actuation of a magnet, (iv) pneumatically displacing the workpiece into a bin, such as by pressurized air, (v) using a robotic arm to pick up and remove the nonconforming workpiece, among other equivalent ways.

For example, a wide variety of reject mechanisms or reject gates are possible. The same gate can be used mechanically but software can be configured to allow the gate to be "RZ—return to zero" or "NRZ—non return to zero" modes. In RZ mode, the gate would stay shut and only open for good parts, then would return to zero for the good part signal. In NRZ mode the gate stays open and waits for the reject part signal, then would shut (return to zero) to reject the part, then open back up to wait for the next reject signal. In this way, the customer can choose which configuration to use. The sorting machine can have multiple sensors that determine whether the part is accepted or rejected. The good parts are blown off into a good chute first. Then, the remaining parts are rejected by a wiper that simply stops the parts from continuing around the dial table, as the rejected part is wiped into the reject bin. Or, the customer can select the opposite, blow the reject parts off and allow the wiper to collect good parts.

While exemplary embodiments are described above, it is not intended that these embodiments describe all possible forms of the invention. Rather, the words used in the specification are words of description rather than limitation, and it is understood that various changes may be made without departing from the spirit and scope of the invention. Additionally, the features of various implementing embodiments may be combined to form further embodiments of the invention.

What is claimed is:

1. A high-speed method of inspecting a stream of manufactured parts and sorting the inspected parts, each of the parts having an optically reflective, exterior bottom surface, the method comprising the steps of:

providing a conveyor subsystem having a forward reach and a return reach and including at least one traveling carrier;

controllably receiving a stream of parts in rapid succession on the at least one traveling carrier at a load station;

utilizing the conveyor subsystem to transfer the stream of parts in rapid succession from the load station to a part inspection station at which the exterior bottom surface of each part has a predetermined position and orientation for optical inspection and from the part inspection station to an unload station;

illuminating the bottom surface of each moving part through its traveling carrier with radiant energy when the part is located at the inspection station to generate reflected radiation signals which are reflected off the exterior bottom surface of each part and which reflected radiation signals travel through its traveling carrier;

forming a bottom image of each illuminated bottom surface from the reflected radiation signals at an imaging location between the forward and return reaches at the inspection station wherein each traveling carrier is made of a material which is substantially transparent to the radiant energy and the reflected radiation signals;
detecting the bottom images at the imaging location;
processing the detected bottom images to identify parts having an unacceptable defect, wherein the unacceptable defect indicates a part parameter or property which fails to fall within a range of acceptable values; and
removing the stream of parts at the unload station after inspection at the inspection station; and
directing parts not identified as having an unacceptable defect to an acceptable part area and directing parts identified as having an unacceptable defect to a defective part area whereby the inspected parts are sorted.

2. The method as claimed in claim 1, wherein the subsystem includes a pair of spaced rollers including a drive roller and actuator assembly for rotatably driving the drive roller and wherein the at least one traveling carrier is a single, transparent, belt which is directed around the rollers when the actuator assembly drives the drive roller.

3. The method as claimed in claim 2, wherein the actuator assembly includes a closed-loop servo motor coupled to the drive roller to rotate the drive roller at a substantially constant angular velocity.

4. The method as claimed in claim 2, wherein the drive roller has a resilient coating or sleeve which drivingly engages the belt.

5. The method as claimed in claim 2, wherein each of the rollers has a resilient coating or sleeve which engages the belt.

6. The method as claimed in claim 2, wherein the rollers include an idler roller spaced from the drive roller and wherein the subsystem includes a take-up device coupled to the idler roller to pull the belt tight.

7. The method as claimed in claim 2, wherein the belt comprises a flexible glass belt having ends and a splice which joins or bonds the ends together.

8. The method as claimed in claim 2, wherein the belt comprises a flexible plastic belt having ends and a splice which joins or bonds the ends together.

9. The method as claimed in claim 1, wherein the subsystem includes a pair of spaced rollers including a drive roller and an actuator assembly for rotatably driving the drive roller and wherein the subsystem further includes at least one band and a plurality of discrete, spaced-apart, traveling carriers supported by the at least one band.

10. The method as claimed in claim 2, wherein the conveyor subsystem includes at least one upper support for supporting a forward reach of the belt between the rollers and a lower support for supporting a lower reach of the belt between the rollers to resist vertical movement of the reaches.

11. The method as claimed in claim 1 wherein the stream of parts is a single-file stream of parts.

12. A high-speed system for inspecting a stream of manufactured parts and sorting the inspected parts, each of the parts having an optically reflective, exterior bottom surface, the system comprising:
a conveyor subsystem having a forward reach and a return reach and including at least one traveling carrier, the at least traveling carrier controllably receiving a stream of parts in rapid succession at a load station, the conveyor subsystem transferring the stream of parts in rapid succession from the load station to a part inspection station at which a bottom surface of each part has a predetermined position and orientation for optical inspection and from the part inspection station to an unload station;
an illuminator configured to illuminate the bottom surface of each part through its traveling carrier with radiant energy when the part is located at the inspection station to generate reflected radiation signals which are reflected off the exterior bottom surface of each part and which reflected radiation signals travel through its traveling carrier;
a lens and detector subsystem configured to form a bottom image of each illuminated bottom surface from the reflected radiation signals at an imaging location between the forward and return reaches at the inspection station and configured to detect the bottom images at the imaging location, wherein each traveling carrier is made of a material which is substantially transparent to the radiant energy and the reflected radiation signals;
at least one processor configured to process the detected bottom images to identify parts having an unacceptable defect, wherein the unacceptable defect indicates a part parameter or property which fails to fall within a range of acceptable values;
at least one device configured to remove the streams of parts from the conveyor subsystem at the unload station after inspection at the inspection station;
a system controller coupled to the conveyor subsystem to control the conveyor subsystem so that the at least one traveling carrier controllably receives and transfers the stream of parts in rapid succession; and
a mechanism including a part sorter for directing parts not identified as having an unacceptable defect to an acceptable part area and directing parts identified as having an unacceptable defect to a defective part area wherein the system controller is coupled to the part sorter and the at least one processor to control the sorting based on the inspecting.

13. The system as claimed in claim 12, wherein the conveyor subsystem includes a pair of spaced rollers including a drive roller and actuator assembly for rotatably driving the drive roller and wherein the at least one traveling carrier is a single, transparent, belt which is directed around the rollers when the actuator assembly drives the drive roller.

14. The system as claimed in claim 13, wherein the actuator assembly includes a closed-loop servo motor coupled to the drive roller to rotate the drive roller at a substantially constant angular velocity.

15. The system as claimed in claim 13, wherein the drive roller has a resilient coating or sleeve which drivingly engages the belt.

16. The system as claimed in claim 13, wherein each of the rollers has a resilient coating or sleeve which engages the belt.

17. The system as claimed in claim 13, wherein the rollers include an idler roller spaced from the drive roller and wherein the conveyor subsystem includes a take-up device coupled to the idler roller to pull the belt tight.

18. The system as claimed in claim 13, wherein the belt comprises a flexible glass belt having ends and a splice which joins or bonds the ends together.

19. The system as claimed in claim 13, wherein the belt comprises a flexible plastic belt having ends and a splice which joins or bonds the ends together.

20. The system as claimed in claim 12, wherein the conveyor subsystem includes a pair of spaced rollers including a drive roller and an actuator assembly for rotatably driving the drive roller and wherein the conveyor subsystem further includes at least one band and a plurality of discrete, traveling carriers supported by the at least one band.

21. The system as claimed in claim 20, wherein the conveyor subsystem includes a pair of spaced, vacuum belts or bands and a plurality of discrete traveling carriers or slides supported between the belts or bands.

22. The system as claimed in claim 13, wherein the conveyor subsystem includes at least one upper support for supporting a forward reach of the belt between the rollers and a lower support for supporting a lower reach of the belt between the rollers to resist vertical movement of the reaches.

23. The system as claimed in claim 12, wherein the stream of parts is a single-file stream of parts.

\* \* \* \* \*

UNITED STATES PATENT AND TRADEMARK OFFICE
CERTIFICATE OF CORRECTION

Page 1 of 1

PATENT NO.       : 9,228,957 B2
APPLICATION NO.  : 14/449361
DATED            : January 5, 2016
INVENTOR(S)      : Nathan Andrew-Paul Kujacznski et al.

It is certified that error appears in the above-identified patent and that said Letters Patent is hereby corrected as shown below:

Claims

Column 13, Line 58, Claim 12:

After "the at least"
Insert -- one --.

Signed and Sealed this
Nineteenth Day of April, 2016

Michelle K. Lee
*Director of the United States Patent and Trademark Office*